(12) United States Patent
Angelos et al.

(10) Patent No.: US 6,919,722 B2
(45) Date of Patent: Jul. 19, 2005

(54) IMAGE QUALITY IMPROVEMENT FOR SENSE WITH LOW SIGNAL REGIONS

(75) Inventors: Elisabeth C. Angelos, Hartland, WI (US); Kevin Franklin King, New Berlin, WI (US); Cynthia Faye Maier, Milwaukee, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 10/605,566

(22) Filed: Oct. 9, 2003

(65) Prior Publication Data
US 2005/0077896 A1 Apr. 14, 2005

(51) Int. Cl.$^7$ .................................................. G01V 3/00
(52) U.S. Cl. ........................................ 324/309; 324/318
(58) Field of Search ................................. 324/309, 307, 324/312, 318; 600/420

(56) References Cited

U.S. PATENT DOCUMENTS

| | | | | |
|---|---|---|---|---|
| 5,497,088 A | | 3/1996 | Hayano et al. | |
| 5,910,728 A | * | 6/1999 | Sodickson | 324/309 |
| 6,326,786 B1 | * | 12/2001 | Pruessmann et al. | 324/312 |
| 6,476,606 B2 | * | 11/2002 | Lee | 324/309 |
| 6,486,671 B1 | | 11/2002 | King | |
| 6,487,435 B2 | * | 11/2002 | Mistretta et al. | 600/420 |
| 6,734,673 B2 | * | 5/2004 | Agrikola | 324/318 |
| 6,771,071 B1 | * | 8/2004 | Wright et al. | 324/318 |
| 6,777,934 B2 | * | 8/2004 | Takahashi et al. | 324/309 |
| 2003/0206016 A1 | * | 11/2003 | Madore | 324/309 |
| 2004/0155652 A1 | * | 8/2004 | Sodickson | 324/309 |

* cited by examiner

*Primary Examiner*—Brij B. Shrivastav
(74) *Attorney, Agent, or Firm*—Artz & Artz, PC

(57) ABSTRACT

An imaging method for an MRI system includes identifying a low signal region within a scanning volume. An overlap calculation of the scanning volume is generated. The low signal region is substantially eliminated from the overlap calculation thereby generating an adjusted overlap structure. A SENSE calculation is generated in response to the adjusted overlap structure.

14 Claims, 4 Drawing Sheets

IMAGE QUALITY IMPROVEMENT FOR SENSE WITH LOW SIGNAL REGIONS

BACKGROUND OF INVENTION

The present invention relates generally to Magnetic Resonance Imaging (MRI) systems, and more particularly, to a method and system for improving image quality.

Magnetic Resonance Imaging (MRI) is a well-known medical procedure for obtaining detailed, one, two and three-dimensional images of patients, using the methodology of nuclear magnetic resonance (NMR). MRI is well suited to the visualization of soft tissues and is primarily used for diagnosing disease pathologies and internal injuries.

Typical MRI systems include a superconducting magnet capable of generating a strong, homogenous magnetic field around a patient or portion of the patient; a radio-frequency (RF) transmitter and receiver system, including transmitter and receiver coils, also surrounding or impinging upon a portion of the patient; a magnetic gradient coil system also surrounding a portion of the patient; and a computer processing/imaging system, receiving the signals from the receiver coil in the form of Fourier transforms and processing the signals into interpretable data, such as visual images.

The superconducting magnet is used in conjunction with a magnetic gradient coil assembly, which is temporally pulsed to generate a sequence of controlled gradients in the main magnetic field during an MRI data gathering sequence.

SENSE (SENSitivity Encoding) is a technique for reducing MRI data acquisition time using multiple surface coil arrays. Generally, it reduces acquisition time by increasing the step size between phase encoding lines of the Fourier transform or by reducing the field of view (FOV). If an object extends outside the reduced field of view, however, aliasing (or wrap-around) occurs in the phase encoding direction. The aliasing includes replications of the object (called aliased replicates) in the phase encoding direction. The spacing of the replications is inversely related to the step size between phase encoding lines of the Fourier transform. Using SENSE to reduce scan time therefore decreases the spacing between aliased replicates in the image. SENSE processing combines aliased multicoil images to remove the aliasing from the final image.

Aliasing can be removed from multicoil images because the aliased replicates ("overlaps") have different coil weighting factors. The expected number of aliased replicates at each pixel is defined as the "overlap structure."SENSE processing calculates an expected overlap structure and then uses (previously measured) surface coil receive B1 fields ("sensitivities") to combine multicoil data to remove aliasing from the final image. Optimal SENSE image quality requires an accurate measurement of the coil sensitivities and a correct calculation of the overlap structure. Inaccuracies in coil sensitivities lead to uncorrected aliasing in the final image. Inaccuracies in the overlap calculation lead to either uncorrected aliasing or increased noise in the final image. Scan regions with low signal ("holes") lead to degraded SENSE image quality because coil sensitivity is hard to measure accurately and attempts to unwrap noise aliasing increase noise in the final image.

The new technique should minimize aliasing degradation in SENSE images and should improve SENSE signal-to-noise-ratio (SNR). The present invention is directed to these ends.

SUMMARY OF INVENTION

In accordance with one aspect of the present invention, an imaging method for an MRI system includes: identifying at least one low signal region within a scanning volume; calculating the overlap structure of the scanning volume (hereafter called an overlap calculation); substantially eliminating the at least one low signal region from the overlap calculation thereby generating an adjusted overlap structure; and generating at least one SENSE calculation in response to the adjusted overlap structure.

In accordance with another aspect of the present invention, an MRI system includes a substantially cylindrical member defining a scanning bore. A coil assembly, including a first coil, is mounted in the scanning bore and is adapted to receive a scan signal and is further adapted to generate an image signal in response to the scan signal. An image reconstructor is adapted to receive the image signal and reconstruct an image therefrom through logic adapted to: identify low signal regions within a scanning volume, generate overlap calculations for the scanning volume, substantially eliminate the low signal regions from the overlap structure calculations thereby generating an adjusted overlap structure, and generate SENSE calculations in response to the adjusted overlap structure. A scan controller is adapted to generate the scan signal.

The advantages of the present invention include improved image quality due to lower noise and less uncorrected aliasing in SENSE scans with low signal regions within the image boundaries. In particular, this invention makes SENSE an efficient technique for coils with large central regions having low coil sensitivity, e.g. those used in a bilateral breast scan.

The present invention itself, together with attendant advantages, will be best understood by reference to the following detailed description, taken in conjunction with the accompanying FIGURES.

BRIEF DESCRIPTION OF DRAWINGS

For a more complete understanding of this invention reference should now be had to the embodiments illustrated in greater detail in the accompanying FIGURES and described below by way of examples of the invention wherein.

DETAILED DESCRIPTION

While the present invention is described with respect to a method for optimizing SENSE image quality by removing low signal regions within the image from the overlap calculation, the present invention may be used when SENSE is applied to many types of MR scanning, including: magnetic resonance spectroscopy systems and magnetic resonance angiography, as will be understood by one skilled in the art.

In the following description, various operating parameters and components are described for one constructed embodiment. These specific parameters and components are included as examples and are not meant to be limiting.

Also in the following description, an MRI system component may include any one of the following: a superconducting magnet, a superconducting magnet support structure, a gradient magnet assembly, an image reconstructor 15 containing the SENSE processing logic, and any other MRI system component known in the art.

The present invention solves the problem of degraded SENSE image quality from low signal regions within an image through including hole locations in the SENSE calculation of an overlap structure. Low (background) signal regions are identified, for example, by thresholding calibration scan data. After these regions are identified, they are assumed not to cause aliasing in the SENSE scan. They are removed from (or not included in) normal overlap calculations, and their (poorly measured) coil sensitivities do not enter the SENSE calculations. In the final SENSE image, the (generally uninformative) hole region is either reconstructed, or "blanked" rather than reconstructed. One skilled in the art will realize that SENSE, as applied in the present invention, reduces scan time by reducing required Fourier measurements.

Figure 1:
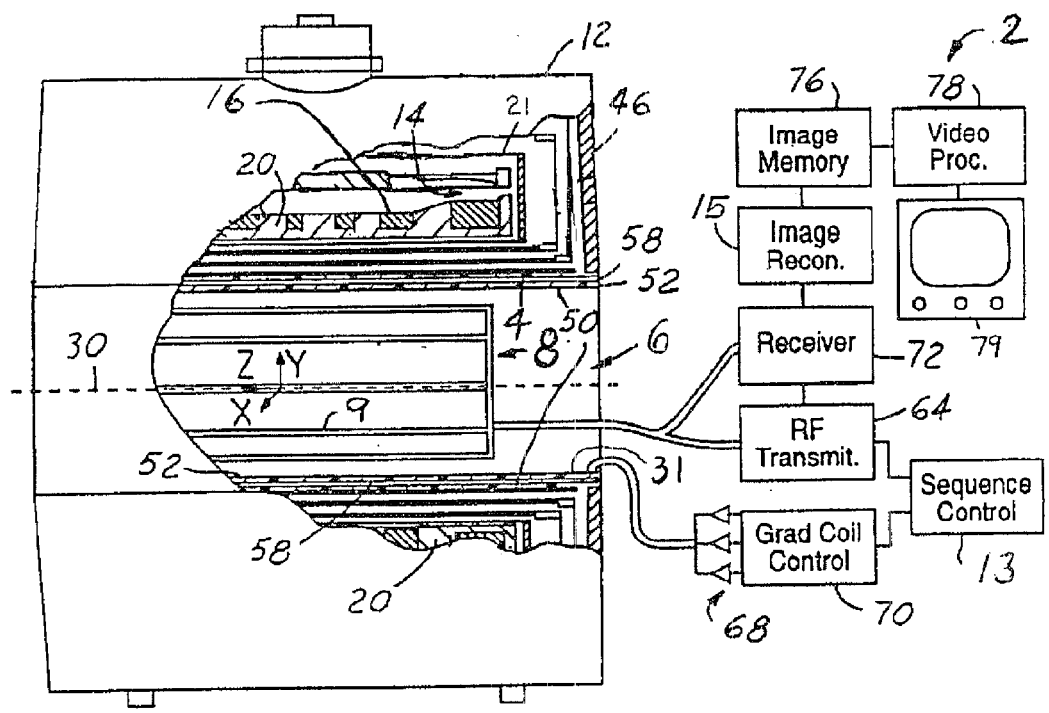
FIG. 1 is a block diagrammatic view of an MRI system in accordance with one embodiment of the present invention.

Referring to FIG. 1, a block diagrammatic view of an MRI system 2 is illustrated. The MRI system 2 includes a substantially cylindrical member 4 that defines a scanning bore 6. The scanning bore 6 includes a coil assembly 8 including a first coil 9 mounted therein. Operation of the first coil 9 is controlled through a scan controller 13 (sequence control), which will be discussed in detail later. An image reconstructor 15 is also coupled to the coil assembly and will be discussed later.

The MRI system 2 further includes a toroidal vacuum vessel 46 that includes the cylindrical member 4 that defines the scanning bore 6 and extends parallel to the longitudinal axis at the center 30 thereof. On a first exterior side 50 of the cylindrical member 4, which is the longitudinal side farthest away from the center 30 of the scanning bore 6, is a magnetic gradient coil assembly 52. A radio-frequency (RF) shield 58 is applied to the magnetic gradient coil assembly 52.

The coil assembly 52, mounted in the scanning bore 6, includes a first coil 31. The coil assembly 52 receives the scan signal and generates an image signal, typically in the form of a discrete set of Fourier transforms, in response to the scan signal.

The MRI system 2 further includes a static magnet structure 12 including a superconducting magnet 14 having a plurality of superconducting magnetic field coils 16 which generate a temporally constant magnetic field along a longitudinal z-axis of the scanning bore 6. The superconducting magnet coils 16 are supported by a superconducting magnet coil support structure 20.

An RF transmitter 64 is connected to the scan controller 13 (sequence controller) and the first coil 31. The scan controller 13 controls a series of current pulse generators 68 via a gradient coil controller 70 that is connected to the magnetic gradient coil assembly 52. The RF transmitter 64, in conjunction with the scan controller 13, generates pulses of radio-frequency signals for exciting and manipulating magnetic resonance through the static magnet structure 12 and in selected dipoles of a portion of the subject within the scanning bore 6. Signals are generated therefrom that are later arranged to generate an image signal or regular image data, as will be understood by one skilled in the art.

The scan controller 13 also generates a calibration scan to identify low signal regions within the scanning volume and therefrom generates a calibration scan signal. The calibration scan is typically conducted prior to the regular scan, as will be understood by one skilled in the art.

The image reconstructor 15, in one embodiment, receives the image signal and the calibration scan signal. This occurs through a radio-frequency receiver 72, connected with the first coil 31, for demodulating magnetic resonance signals emanating from an examined portion of a subject. The image reconstructor 15 reconstructs the received magnetic resonance signals (image signal) into an electronic image representation that is stored in an image memory 76.

In the present embodiment, the image reconstructor 15 receives the image signal and reconstructs an image therefrom through logic that: generates overlap calculations, substantially eliminates low signal regions from the overlap calculations thereby generating an adjusted overlap structure, and generates SENSE calculations in response to the adjusted overlap structure.

The image reconstructor 15 further receives the calibration scan signal and substantially eliminates low signal regions from the overlap calculations in response thereto, as was previously mentioned.

SENSE reconstruction through SENSE calculations, in the Cartesian case, is conducted by first creating an aliased image for each array element using a discrete Fourier transform (DFT).

The second step is to create a full-FOV image from the set of intermediate images. This involves decomposing the signal superposition underlying the fold-over effect. That is, for each pixel in the reduced FOV, the signal contributions from a number of positions in the full FOV are separated. These positions are separated by a distance equal to the size of the reduced FOV.

An image reconstruction device, such as a video processor 78 converts stored electronic images into an appropriate format for display on a video monitor 79.

Figure 2:
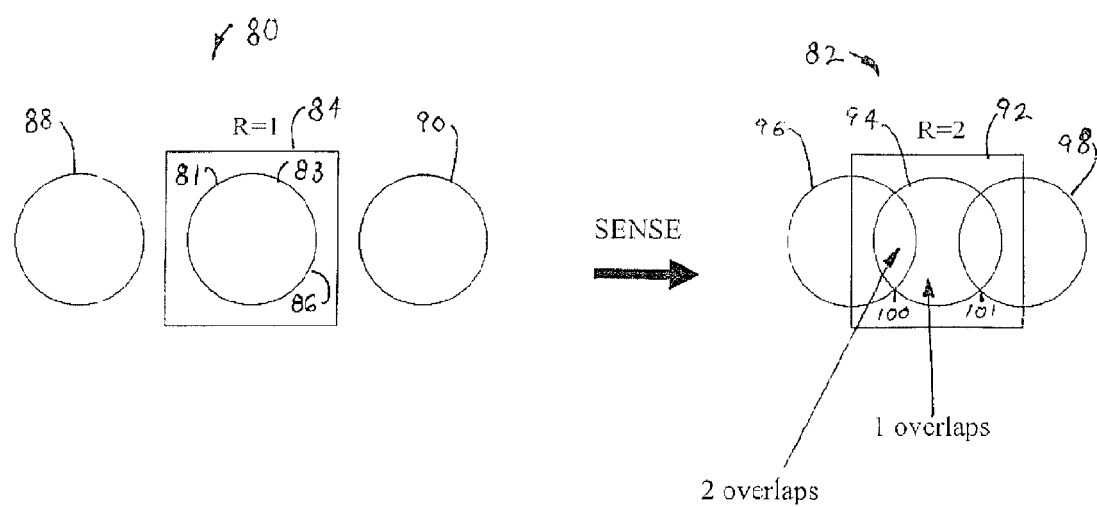
FIG. 2 is an output diagram of a scanned object prior to reconstruction in accordance with another embodiment of the present invention.

Referring to FIG. 2, a data sample 80 lacking SENSE calculations, and a data sample 82 of the same object, using SENSE calculations, is illustrated. FIG. 2 further illustrates the use of edge information in the present invention to improve image quality. The edge information is obtained through a separate scan, e.g. a calibration scan, which senses the edge 81 of the circle 83. Essentially, edge information improves SENSE image quality (IQ) by decreasing the number of overlaps used in the SENSE calculations for areas that do not have aliasing.

The prescribed field-of-view (FOV) 84 of the sample 80 surrounds one of the aliased replicates 86. The two closest aliased replicates 88, 90 are illustrated on either side of the FOV 84. The scenario illustrated by 80 does not use SENSE (no field of view reduction). In this scenario the aliased replicates are far enough apart so that there is no overlapping of elements.

The SENSE data sample 82 is illustrated having the FOV 92 surround one Fourier transform element 94 and two of the closest aliased replicates 96, 98. The scenario illustrated by 82 uses spacing in the Fourier domain twice as far apart As the scenario illustrated by 80. Resultantly, scan time is reduced but the aliased replicates are closer. Two sections 100, 101 include two aliased replicates, and the remainder of the object is illustrated with one replicate.

In other words, there are two replicates at every pixel in a calculation that did not consider edges. By including edges, SENSE processing only sees one replicate in several regions, including the center of the image (dataset 94).

Figure 3:
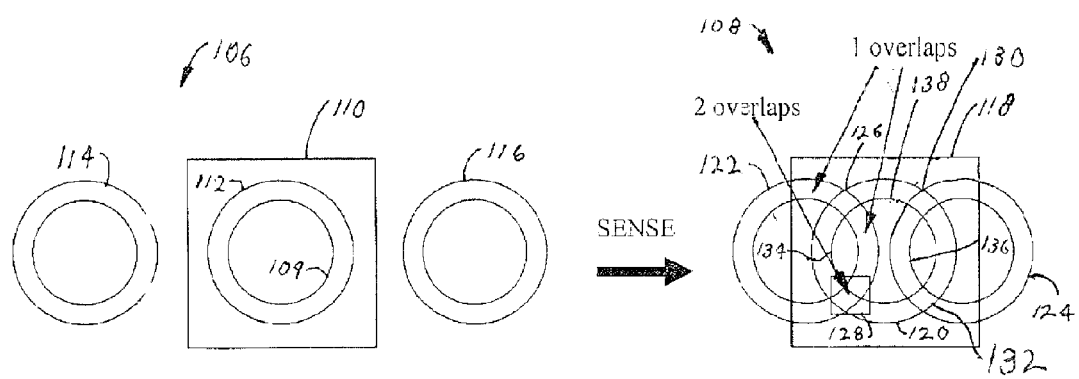
FIG. 3 is an alternate output diagram of a scanned object prior to reconstruction in accordance with another embodiment of the present invention.

Referring to FIG. 3, a data sample 106 lacking SENSE calculations, and a data sample 108 of the object (which is here illustrated as an object including a central hole 109), using SENSE calculations, is illustrated. The central hole 109 is a region wherefrom a low signal is generated. Low signal is generated from regions having, for example: low coil sensitivity, no tissue, or a signal suppression from the pulse sequence. The prescribed field-of-view (FOV) 110 of the sample 106 surrounds one of the aliased replicates 112. The two closest aliased replicates 114, 116 are illustrated on either side of the FOV 110. In the scenario illustrated the adjacent aliased replicate spacing is far enough apart so that there is no overlapping of elements.

The SENSE data sample 108 is illustrated having the FOV 118 surround one aliased replicate 120 and two of the closest aliased replicates 122, 124. The spacing in the Fourier domain twice as far apart as the scenario illustrated by 106. Resultantly, scan time is reduced but the aliased replicates are closer. Four sections 126, 128, 130, 132 include two aliased replicates, and the remainder of the object is illustrated with one replicate and holes 134, 136, 138 occurring between the overlap sections 126, 128, 130, 132.

When there are low signal regions within the object, the number of aliased replicates is decreased in additional regions in the SENSE image. In the above example, considering holes and edges reduces the number of aliased replicates to one everywhere except the four small square regions 126, 128, 130, 132 where the rings 120, 122, 124 overlap.

When holes are accounted for in SENSE calculations, the number of aliased replicates is reduced in areas where hole and signal regions overlap. Since SENSE image quality is related to overlap structure, these areas can have image quality similar to that produced by longer SENSE scans (without holes), which produce less aliasing for correction.

SENSE, in the present invention, decouples coils in a simultaneous acquisition of two separate volumes, such as the two sagittal volumes in a bilateral breast scan. For these scans, SENSE processing is setup as a single large volume with a discarded central region. The present invention improves image quality for this type of scan by treating the central region as a hole.

Figure 4:
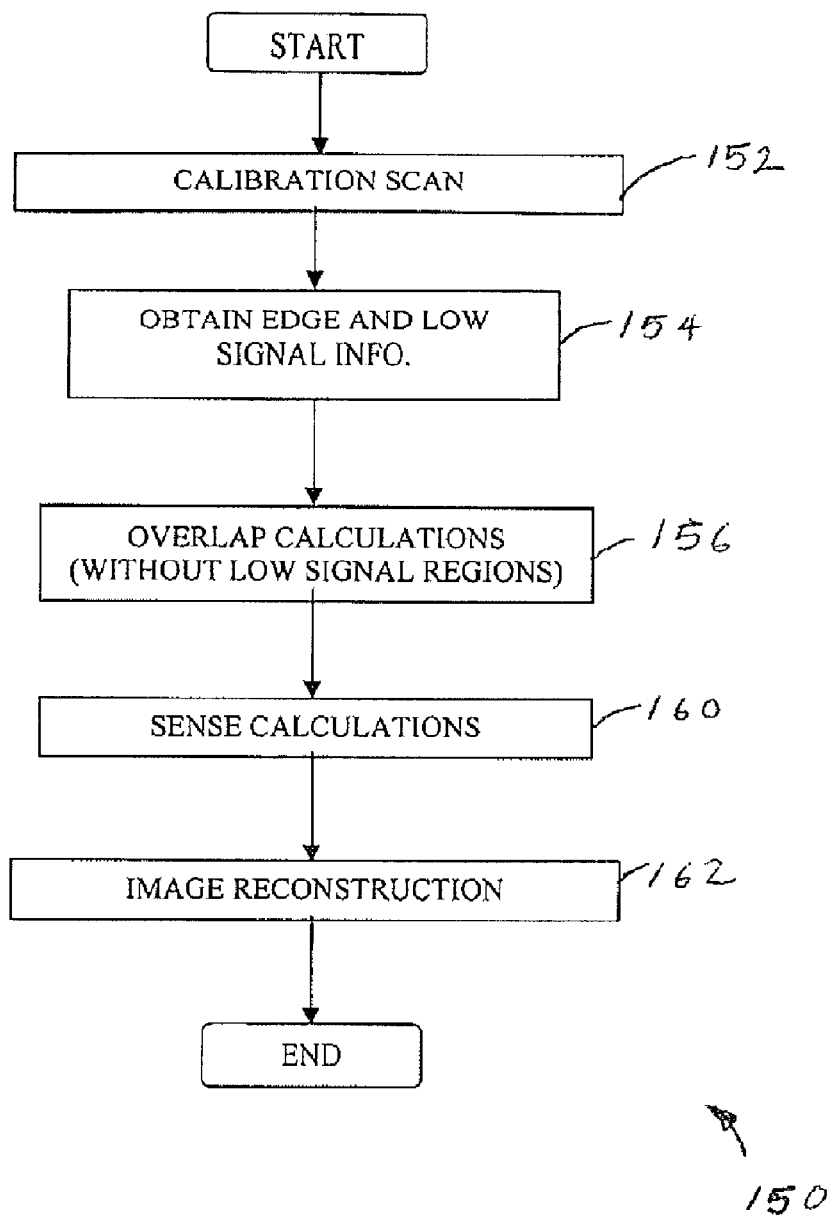
FIG. 4 is a logic flow diagram of a method for MRI scanning in accordance with another embodiment of the present invention.

Referring to FIG. 4, a logic flow diagram 150 of a method for MRI scanning, in accordance with another embodiment of the present invention, is illustrated.

Logic starts in operation block 152 where a (thresholding) calibration scan is run either in response to a signal from a scan operator or through a preset program within the scan controller.

In operation block 154, low signal regions are identified through, for example, the thresholding calibration scan data. After these regions are identified, they are assumed not to cause aliasing in the SENSE scan.

In operation block 156, low signal regions are removed from (or not included in) overlap calculations, and the respective coil sensitivities do not enter the SENSE calculations.

In operation block 160, SENSE calculations are generated during a SENSE scan operation, and in the final SENSE image, in operation block 162, the hole regions are either reconstructed using a SENSE calculation, or blanked rather than reconstructed.

In operation, a method for MRI scanning includes generating a calibration scan of a scanning volume thereby obtaining edge information. Low signal regions are identified within the scanning volume. Overlap calculations of the scanning volume are generated. Low signal regions are substantially eliminated from the overlap calculations thereby generating an adjusted overlap structure. A SENSE scan is then conducted, and SENSE calculations are generated in response to the adjusted overlap structure. An image of the scanning volume is reconstructed in response to the SENSE calculations.

The above-described steps are meant to be an illustrative example. The steps may be performed synchronously or in a different order depending upon the application.

The above-described apparatus, to one skilled in the art, is capable of being adapted for various purposes and is not limited to the following systems: MRI systems, magnetic resonance spectroscopy systems, and other applications where image quality is an issue following scan operations. The above-described invention may also be varied without deviating from the spirit and scope of the invention as contemplated by the following claims.

What is claimed is:

1. An MRI system comprising:
    a substantially cylindrical member defining a scanning bore;
    a coil assembly mounted in said scanning bore and comprising a first coil, said coil assembly adapted to receive a scan signal, said coil assembly further adapted to generate an image signal in response to said scan signal;
    an image reconstructor adapted to receive said image signal and reconstruct an image therefrom through logic adapted to: generate overlap calculations, substantially eliminate low signal regions from said overlap calculations thereby generating an adjusted overlap structure, and generate SENSE calculations in response to said adjusted overlap structure; and
    a scan controller adapted to generate said scan signal.

2. The system of claim 1 wherein said scan controller is further adapted to generate a calibration scan to identify low signal regions within said scanning volume and therefrom generate a calibration scan signal.

3. The system of claim 2 wherein said image reconstructor is further adapted to receive said calibration scan signal and substantially eliminate low signal regions from said overlap calculations in response thereto.

4. An imaging method for an MRI system comprising:
    identifying at least one low signal region within a scanning volume;
    generating an overlap calculation of said scanning volume;
    substantially eliminating said at least one low signal region from said overlap calculation thereby generating an adjusted overlap structure; and
    generating at least one SENSE calculation in response to said adjusted overlap structure.

5. An imaging method as in claim 4 further comprising generating a calibration scan of a scanning volume thereby obtaining edge information.

6. An imaging method as in claim 4 further comprising reconstructing an image of said scanning volume in response to said SENSE calculations.

7. An imaging method as in claim 4 wherein generating at least one SENSE calculation in response to said adjusted overlap structure further comprises generating a SENSE scan responsive to said adjusted overlap structure; and
    reconstructing an image of said scanning volume in response to said SENSE scan.

8. An imaging method as in claim 7 wherein reconstructing further comprises reconstructing using a full SENSE calculation.

9. An imaging method as in claim 7 wherein reconstructing further comprises blanking said at least one low signal region.

10. An imaging method as in claim 4 wherein identifying at least one low signal region within a scanning volume further comprises identifying at least one low signal region through a thresholding calibration scan.

11. An imaging method for an MRI system comprising:

generating a calibration scan of a scanning volume thereby obtaining edge information;

identifying low signal regions within said scanning volume;

generating overlap calculations of said scanning volume;

substantially eliminating said low signal regions from said overlap calculations thereby generating an adjusted overlap structure;

generating a SENSE scan responsive to said adjusted overlap structure; and reconstructing an image of said scanning volume in response to said SENSE scan.

12. An imaging method as in claim 11 wherein reconstructing further comprises reconstructing using a full SENSE calculations.

13. An imaging method as in claim 11 wherein reconstructing further comprises blanking said low signal regions.

14. An imaging method as in claim 11 wherein identifying said low signal regions within said scanning volume further comprises identifying said low signal regions through a thresholding calibration scan.

* * * * *